(12) United States Patent
Kamboh et al.

(10) Patent No.: US 6,203,980 B1
(45) Date of Patent: Mar. 20, 2001

(54) IDENTIFICATION OF APOLIPOPROTEIN H MUTATIONS AND THEIR DIAGNOSTIC USES

(75) Inventors: M. Ilyas Kamboh; Dharambir K. Sanghera, both of Pittsburgh; Susan Manzi, Wexford, all of PA (US)

(73) Assignee: University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 09/016,390

(22) Filed: Feb. 2, 1998

(51) Int. Cl.$^7$ .............................. C12Q 1/68; C12P 19/34; C07H 21/04
(52) U.S. Cl. ............................. 435/6; 435/91.2; 435/810; 536/24.31; 536/24.33
(58) Field of Search ............................... 435/6, 91.2, 810; 536/24.31, 24.33

(56) References Cited

PUBLICATIONS

Medhi et al. American Journal of Human Genetics. 61: A209, abstract 1189, Oct. 1997.*
Lozier, J., et al., *Proc. Natl. Acad. Sci. USA* 81: 3640 (1984).
Kristensen, T., et al., *FEBS Lett.* 289: 183 (1991).
Medhi, H., et al., *Gene* 108: 293 (1991).
Steinkasserer, A., et al., *Biochem. J.* 277: 387 (1991).
Davie, E.W., et al., *Cold Spring Harbor Symposium on Quantitative Biology* vol. Li pp. 509–514 (1986).
Ichinose, A., et al., *J. Bioll Chem.* 265: 13441 (1990).
Kristensen, T., et al., *Federation Prac.* 46: 2463 (1987).
Kato, H., et al., *Biochemistry* 30: 11687 (1991).
Aoyama, Y., et al, *Nucl. Acids Res.* 17: 6401 (1989).
Nonaka, M., et al., *Genomics* 13: 1082 (1992).
Sellar, G.C., et al., *Biochem, Biophys. Res. Commun.* 191: 1288 (1993).
Kamboh, M.I., et al., *Adv. Lipid Res.* 1: 9 (1991).
Roubey, R.A.S., et al., *Blood* 84: 2854 (1994).
Shousboe, I., et al., *Blood* 66: 1086 (1985).
McNeil, H.P., et al., *Prac .Natl. Acad. Sci USA* 87 4120 (1990).
Galli, M., et al., *Lancet* 335: 1544 (1990).
Jones, J.V., et al., *J. Rheumatol.* 19 1397 (1992).
Hunt, J.E., et al., *Lupus* 1: 75 (1992).
Cabral, A.R., et al., *J. Autoimmunity* 5: 787 (1992).
Matsuura, E., et al., *J. Exp Autoimmunity* 5: 787 (1992).
Arvieux, J., et al., *Clin. Exp. Immunol.* 95: 310 (1994).
Cabiedes, J., et al., *J. Rheumatol.* 22: 1899 (1995).
Cabral, A.R., et al., *J. Rheumatol.* 22: 1894 (1995).
Hunt, J.E., et al., *Prac. Natl. Acad. Sci. USA* 90: 2141 (1993).
Hunt, J.E., et al., *J. Immunol.* 152: 653 (1994).
Kamboh, M.I., et al., *Am. J. Hum Genet.* 42 452 (1988).
Wagenknecht, D.R., et al., *Thromb. Haemost.* 69: 361 (1993).
Kamboh, M.I., et al., *Hum. Genet..* 95: 385 (1995).
Sanghera, D.K., et al., *Hum. Genet.* 106: 57 (1997).
Orita, M., et al., *Genomics* 5: 874 (1989).
Steinkasserer, A., et al., *Hum. Genet* 91: 401 (1993).
Steinkasserer, A., et al., *FEBS Lett.* 313: 192 (1992).
Sanghera, D.K., et al., *Human Molecular Genetics*: 6(2): 311 (1997).

\* cited by examiner

*Primary Examiner*—Carla J. Myers
(74) *Attorney, Agent, or Firm*—Reed Smith LLP

(57) ABSTRACT

Structural mutations in the fifth domain of apolipoprotein H have been identified which affect phospholipid binding and which predict protection from systemic lupus erythematosis which can be used in genetic analysis.

26 Claims, 5 Drawing Sheets

IDENTIFICATION OF APOLIPOPROTEIN H MUTATIONS AND THEIR DIAGNOSTIC USES

ACKNOWLEDGMENT

The present invention was developed in part with government support under grant number HL 54900 awarded by the National Institutes of Health. The government has certain rights in this invention.

FIELD OF THE INVENTION

The present invention relates generally to the identification of structural mutations of apolipoprotein H (β2-glycoprotein I), and their relationship to systemic lupus erythematosus and phospholipid binding. The present invention also relates to the molecular basis of a genetically determined polymorphism for apolipoprotein H is protein. In particular the present invention relates to the use of genetic analysis of apolipoprotein H to predict protection from systemic lupus erythematosus ("SLE") and to predict the production of antiphospholipid antibodies in SLE patients. The methods of the present invention allow for potential diagnostic and th erapeutic uses of DNA material that incorporate such mutations.

BACKGROUND OF THE INVENTION

Apolipoprotein H ("apoH" for protein; "APOH" for gene), also referred to as β2-glycoprotein I, is a single chain glycoprotein of 326 amino acids as determined directly from purified protein (Lozier, J., et al., *Proc. Natl. Acad. Sci. USA* 81:3640 (1984)) and was subsequently confirmed by deduced am ino acid sequence by cDNA cloning and sequencing (Kristensen, T., et al., *FEBS Lett.* 289:183 (1991); Mehdi, H., et al., *Gene* 108:293 (1991); and Steinkasserer, A., et al., *Biochem. J.* 277:387 (1991)). The CDNA sequence predicts 345 amino acids which include 19 hydrophobic signal peptide residues not present in the mature protein. The apoH protein shows extensive internal homology with five consecutive homologous segments of about 60 amino acids each. These segments are referred to variously as: GP-I domains (because they were first found in β2-glycoprotein 1 as described by Davie, E. W., et al., *Cold Spring Harbor Symposium on Quantitative Biology Vol. Li* pp. 509–514 (1986), Sushi domains as described by Ichinose, A., et al., *J. Biol. Chem.* 265:1341 (1990), SCRs (short consensus repeats), or CCP (complement control protein) repeats (Kristensen, T., et al., *Federation Proc.* 46:2463 (1987)). Such domains or repeats are commonly found in a number of complement component proteins, as well as in non-complement proteins. Based upon the predicted structure of the apoH protein from its cDNA sequence, there are 22 cysteine residues in human apoH. These positions are conserved in the apoH protein of bovine (Kato, H., et al., *Biochemistry* 30:11687 (1991)), rat (Aoyama, Y., et al., *Nucl. Acids Res.* 17:6401 (1989)), mouse (Nonaka, M., et al., *Genomics* 13:1082 (1992)) and dog (Sellar, G. C., et al., *Biochem. Biophys. Res. Commun.* 191:1288 (1993)). The apoH proteins of these species also consist of 5 GP-I domains as in humans. The human APOH gene has been localized on chromosome 17q23-24 and is expressed primarily in the liver (Steinkasserer, A., et al., *Biochem. J.* 277:387 (1991).

ApoH has been implicated in a variety of physiologic pathways including lipoprotein metabolism as described by Kamboh, M. I., et al., *Adv. Lipid Res.* 1:9 (1991), coagulation as described by Roubey, R. A. S., et al., *Blood* 84:2854 (1994) and in the production of antiphospholipid autoantibodies ("aPA") as described by Schousboe, I., et al., *Blood* 66:1086 (1985). ApoH also binds to platelets, mitochondria, heparin, DNA, and anionic phospholipids and has been shown to be involved in the blood coagulation pathway, platelet aggregation, and prothrombinase activity of platelets. ApoH is considered to be a required cofactor for anionic phospholipid antigen binding by the aPA found in sera of many patients with systemic lupus erythematosus ("SLE") and primary antiphospholipid syndrome ("APS") (see, for example, McNeil, H. P., et al., *Proc Natl. Acad. Sci USA* 87:4120 (1990); Galli, M., et al., *Lancet* 335: 1544 (1990); and Jones, J. V., et al., *J. Rheumatol.* 19:1397 (1992)), but it does not seem to be required for the reactivity of aPA associated with infections as described by Hunt, J. E., et al., *Lupus* 1:75 (1992). These studies suggest that the apoH-phospholipid complex forms the antigen to which aPA are directed as described by Cabral, A. R., et al., *J. Autoimmunity* 5:787 (1992) and Matsuura, E., et al., *J. Exp. Med.* 179:457 (1994). Recently, however, the presence of autoantibodies to phospholipid-free apoH has been shown in patients with primary APS (see, for example, Arvieux, J., et al., *Clin. Exp. Immunol.* 95:310 (1994); Cabiedes, J., et al., *J. Rheumatol.* 22:1899 (1995); Cabral, A. R., et al., *J. Rheumatol.* 22:1894 (1995)).

Although the structural domains of apoH which bind to anionic phospholipids are unknown, studies have proposed that the expressed fifth domain of apoH carries the potential binding site for anionic phospholipids and anticardiolipin antibodies ("aCL") and it may be critical for lipid-protein interaction (see, Hunt, J. E., et al., *Proc. Natl. Acad. Sci. USA* 90:2141 (1993) and Hunt, J. E., et al., *J. Immunol.* 52:653 (1994). As stated above, the precise location of the apoH site which binds to anionic phospholipids has not been delineated prior to the present invention.

ApoH exhibits genetically determined structural polymorphism as revealed by isoelectric focusing ("IEF") and immunoblotting as described by Kamboh, M. I., et al., *Am. J. Hum. Genet.* 42:452 (1988). Three common alleles, APOH*1, APOH*2 and APOH*3 control the expression of six phenotypes, designated 1-1, 2-1, 2-2, 3-1, 3-2 and 3-3. A fourth allele, APOH*4, has been observed only in populations of African ancestry. Three IgG1$_K$ monoclonal antibodies ("mAb"), 3G9, 1B4, and 3D11, have been produced to human apoH as described by Wagenknecht, D. R., et al., *Thromb. Haemost.* 69:361 (1993). In contrast to mAb 3G9 and 1B4, which recognize free and phospholipid-bound apoH and which react with all apoH allelic isoforms, the mAb 3D11 recognizes only one form of the APOH*3 allele, called APOH*3$^W$ (allele called APOH*3$^B$ not recognized), that does not bind to anionic phospholipids (see, Kamboh, M. I., et al., *Hum. Genet.* 95:385 (1995)). Therefore, plasma samples reacting with mAb 3D11 could be either homozygous H3$^W$/H3$^W$ or heterozygous H3$^W$/H3$^B$.

Systemic lupus erythematosus ("SLE") is a chronic inflammatory disease affecting the connective tissues with a pathogenesis believed to involve abnormalities of the immune system. SLE is associated with the generation of numerous autoantibodies directed against various cell components. This autoimmune disorder affects women more than it does men. Overall reported prevalence of SLE is approximately 50–75 per 100,000. The incidence of SLE peaks during the ages of 15 and 45 and this excess is attributable to females, who outnumber males by 5:1. The female to male frequency ratio is particularly striking between ages 15 and 45, in that it reaches 12–15:1.

Antiphospholipid autoantibodies are a heterogeneous group of autoantibodies including most commonly a lupus anticoagulant ("LAC") and anticardiolipin antibodies ("aCL") which are directed against negatively charged phospholipids. The prevalence of aCL in the general population have been reported to be as low as 1.7%. In contrast, the frequency of antiphospholipid autoantibodies (including aCL and LAC) in SLE patients varies between 20 and 60%. Although a high frequency of patients with SLE may have these autoantibodies, only approximately one-third will have a clinical manifestation associated with the presence of these autoantibodies, including a thrombotic event, fetal loss, or thrombocytopenia. The presence of antiphospholipid autoantibodies in SLE patients has been associated with recurrent deep vein thrombosis and other thrombotic complications, including pulmonary, renal, and retinal thrombosis, as well as Budd-Chiari syndrome. In addition, associations between antiphospholipid autoantibodies and arterial thrombosis including cerebral, retinal and peripheral artery have been reported. Recurrent fetal losses, usually occurring in the second and third trimester, felt to be due in part to thrombosis of the placental vessels and subsequent infarction resulting in placental insufficiency and ultimately fetal loss have also frequently been reported in association with antiphospholipid autoantibodies.

Due to the critical nature of the SLE disease, there is an urgent need for better diagnostic methods for early detection of the disease, and screening methods to detect genetic carriers of the disease. Additionally, there is a critical need for an effective treatment, and even more preferably, a cure for the underlying genetic defect. There further remains a need for means to understand the underlying mechanism for the production of antiphospholipid autoantibodies in SLE patients. All these needs are addressed by the present determination of the structural mutations in the APOH gene which affect binding of negatively charged phospholipids and the determination that one of those mutations provides protection from the occurrence of SLE.

The disclosures of all publications referenced above and throughout this application below are hereby incorporated in their entirety herein by reference.

SUMMARY OF THE INVENTION

According to the present invention two relatively common structural mutations at codons 316 and 306 in the fifth domain of apoH have been identified which render apoH unable to bind to negatively charged phospholipids, in particular, phosphatidylserine ("PS"). The missense mutation at codon 316 (TGG→TCG) replaces Trp-316 with Ser-316 and disrupts the integrity of four highly conserved hydrophobic amino acids sequence at positions 313–316, which is a potential protein-lipid hydrophobic interaction site. The missense mutation at codon 306 (TGC→GGC) involves the substitution of Cys-306 by Gly-306 which causes the disruption of a disulfide bond between Cys-281 and Cys-306 and affects the normal configuration of the fifth domain of apoH that appears to be critical for clustering positively charged amino acids along with the four hydrophobic amino acids sequence. ApoH from the two homozygotes (Ser-316/Ser-316) and apoH from all seven compound heterozygotes (Ser-316/Gly-306) failed to bind to PS; all heterozygotes at one or the other sites and wild type showed normal PS binding. These data indicate that the fifth domain of apoH harbors the lipid binding region. An estimated 2 million Caucasians in the United States, who are compound heterozygotes for the two mutations, may be precluded from producing apoH-dependent antiphospholipid autoantibodies and thereby may be precluded from suffering related thrombotic and other disorders. Additionally, the codon 306 mutation by itself appears to provide protection against SLE.

The present invention provides nucleic acid sequences, genes, polypeptides, genetic screening methods, diagnostic methods and kits, and the basis for methods of treating SLE patients.

Accordingly, it is primary object of the present invention to identify structural mutations in the human apolipoprotein H gene that affect binding of apolipoprotein H protein to negatively charged phospholipid.

Still another object of the present invention is to identify structural mutations in the apolipoprotein H gene that affect binding of the apolipoprotein H protein to phosphatidylserine.

Yet another object of the present invention is to provide amplification primers for amplifying mutations in the apolipoprotein H gene that affect binding to negatively charged phospholipid.

Still another object of the present invention is to provide amplification primers for amplifying the point mutation of the human apolipoprotein H gene at codon 316 (TGG→TCG) which replaces Trp316 with Ser316.

Yet another object of the present invention is to provide amplification primers for amplifying the point mutation of the apolipoprotein H gene at codon 306 (TGC→GGC) which replaces Cys306 with Gly306.

Yet another object of the present invention is to provide amplification primers for amplifying the point mutation of the apolipoprotein H gene at codon 88 (AGT→AAT) which replaces Ser88 with Asn88.

Still yet another object of the present invention is to identify a mutation in the apolipoprotein H gene which provides protection against the occurrence of systemic lupus erythematosus.

Yet another object of the present invention is to provide methods and kits for detecting the mutations of the apolipoprotein H gene at codon 316 and codon 306 in the fifth domain of apoH.

Still yet another object of the present invention is to provide therapeutic materials and methods for individuals afflicted with SLE based on missense mutations in the fifth domain of apoH.

These and other objects of the present invention are achieved by one or more of the following embodiments.

In one aspect, the invention features a method to determine the presence or absence of a mutation in an individual that protects against the occurrence of systemic lupus erythematosus, comprising the steps of:
 a) obtaining genomic DNA from the individual;
 b) amplifying the genomic DNA with a primer pair for exon 7 of the apolipoprotein H gene; and
 c) determining the presence or absence of a missense mutation at codon 306 of exon 7 of the apolipoprotein H gene from the codon TGC to GGC.

In another aspect, the invention features a method to determine the presence or absence of missense mutations in the fifth domain apolipoprotein H gene at codon 306 (TGC→GGC) and codon 316 (TGG→TCG) of an individual that render apolipoprotein H protein unable to bind to negatively charged phospholipid, comprising the steps of:
 a) obtaining genomic DNA from the individual;
 b) amplifying the genomic DNA with a primer pair for exon 7 for codon 306;
 c) amplifying the genomic DNA with a primer pair for exon 8 for codon 316; and
 d) determining the presence or absence of the mutations at codon 306 of exon 7 and codon 316 of exon 8 in the fifth domain of said apolipoprotein H gene.

In yet another aspect, the invention features A method of treating an individual that has systemic lupus erythematosus comprising:

administering to the individual a therapeutically effective amount of at least one compound that prevents apolipoprotein H from binding to negatively charged phospholipid and which thereby prevents production of antiphospholipid autoantibodies in the individual and a pharmaceutically acceptable carrier.

In a preferred embodiment, the mutation of interest is detected by DNA sequencing, restriction analysis, and restriction fragment length polymorphism analysis.

Other features and advantages of the invention will be apparent from the following description of the preferred embodiment, and from the claims.

The disclosures of all publications referenced above and hereafter are hereby incorporated in their entirety herein by reference.

DESCRIPTION OF THE DRAWINGS

In FIG. 1B, the uncut fragment of 148 bp corresponds to the Trp-316 wild type and the two cut fragments of 86 bp and 62 bp correspond to the Ser-316 mutant type on 2% Nusieve agarose gel. Sample numbers 1, 6: Trp-316/Trp-316; Sample numbers 2, 3: Trp-316/Ser-316; Sample numbers 4, 5: Ser-316/Ser-316. A minor band at position 148 bp in samples 4 and 5 indicates incomplete digestion of the 148 bp fragment.

FIG. 3B shows that while fragment sizes of 124 bp, 112 bp and 83 bp correspond to the Cys-306 wild type, fragment sizes of 124 bp, 112 bp and 51 bp correspond to the Gly-306 mutation. Sample numbers 1, 3: Cys-306/Cys-306; Sample numbers 2, 4, 5: Cys-306/Gly-306. The line on the far right contains a DNA marker.

FIG. 4A shows the amino acid sequence (243–326) of the fifth domain of human apoH. The three disulfide bond linkages between Cys-245 to Cys-296, Cys-281 to Cys-306, and Cys-288 to Cys-326 are indicated by lines in the figure. The position of cysteine residues are given below the amino acid sequence. Arrows at 306 and 316 indicate the mutation sites. FIG. 4B shows the normal configuration of the fifth domain with all three disulfide bonds intact. The position of all six cysteine residues are labeled. Circles indicate the mutation sites at codons 306 and 316. FIG. 4C shows a possible model of the predicted configuration of the fifth domain after the loss of the disulfide bond between Cys-281 to Cys-306 due to the substitution of Cys-306 by Gly-306.

FIG. 5A shows direct sequencing of double-stranded DNA. Sequence on the left corresponds to a heterozygote carrier (1-2) and on the right corresponds to a homozygote (1-1), with the mutation. FIG. 5B shows restriction analysis with Tsp509I which shows the uncut fragment of 207 bp, which corresponds to the wild type and two cut fragments of 144 bp and 63 bp which correspond to the APOH*1 type on 2% Nusieve agarose gel. Lanes 1 and 3 are homozygous for the APOH*1 allele, lane 4 is homozygous for the APOH*2 allele, and lane 2 is heterozygous for the two alleles.

DETAILED DESCRIPTION OF THE INVENTION

I. DEFINITIONS

Figures 1A, 1B:
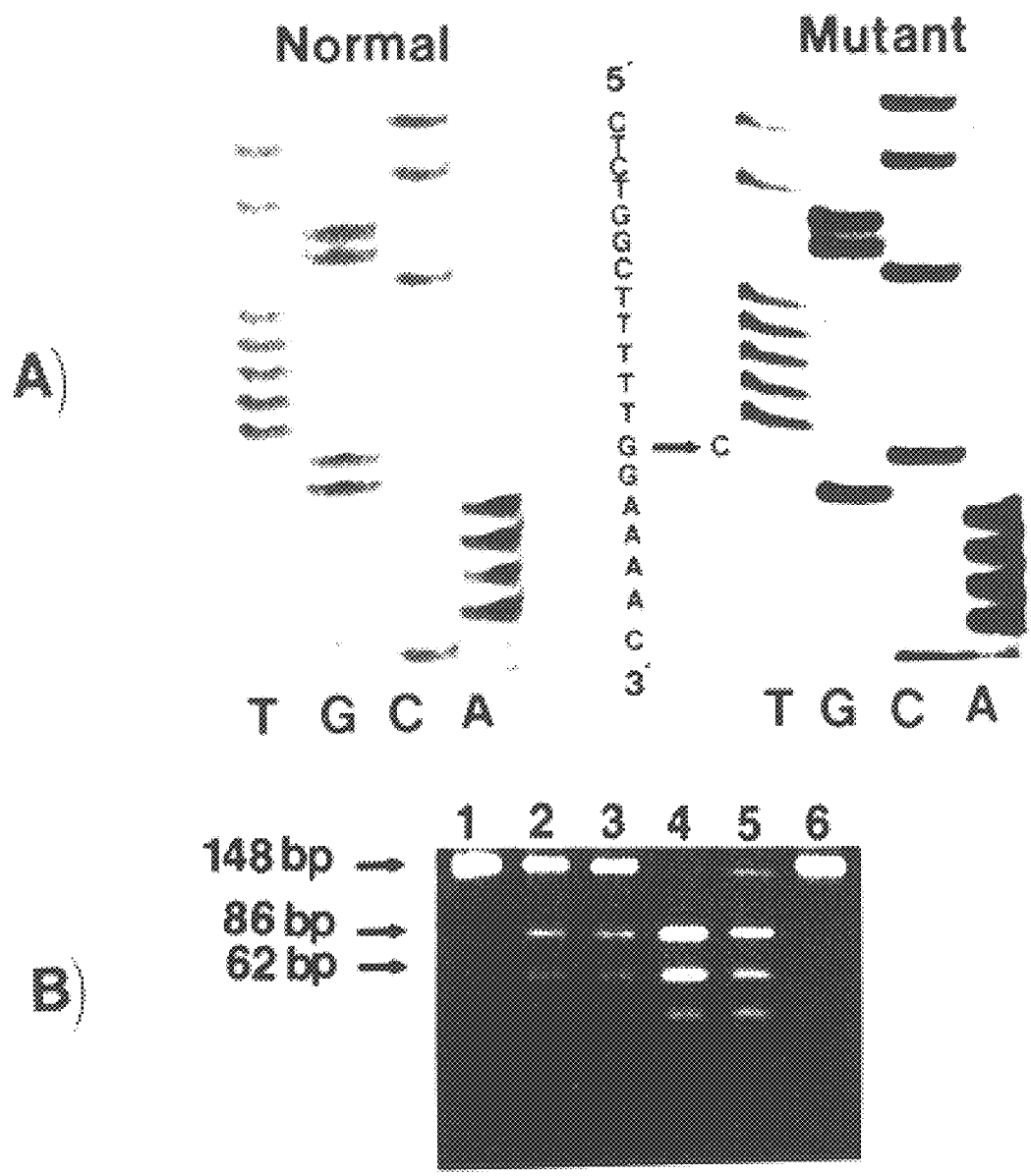
FIGS. 1A and 1B are photographs showing identification of a point mutation at codon 316 (TGG→TCG) by direct sequencing of double-stranded DNA (FIG. 1A), and by restriction analysis with BstBI (FIG. 1B).

As used herein apolipoprotein H ("apoH") refers to a member of a class of proteins associated with a lipid molecule that is involved in lipid metabolism, coagulation, and in the production of antiphospholipid autoantibodies ("aPA").

The terms "antiphospholipid autoantibodies" or "aPA" are used herein to mean a group of antibodies produced against an individual's own negatively charged phospholipids. Lupus anticoagulant ("LAC") and anticardiolipin antibodies ("aCL") are common members of the group. There is a high frequency of antiphospholipid autoantibodies in systemic lupus erythematosus ("SLE") patients as compared to the general population. Thrombotic complications and fetal loss are associated with the presence of aPA's in SLE patients. "Systemic lupus erythematosus," "SLE," or "lupus" refer to an autoimmune disease of the connective tissues/joints characterized by autoantibody production against cellular components.

"Structural polymorphism" means a DNA mutation in a gene that causes a change in the amino acid coded thereby.

"Missensense mutation" and "point mutation" refer to a DNA mutation caused by a single nucleotide change. In apoH, missense mutations at codons 306, 316, and 88 direct the incorporation of a different amino acid.

II. METHODS

The present invention relates to the discovery of a new "protective" gene for systemic lupus erythematosus ("SLE") and for the production of antiphospholipid antibodies which can be used for genetic screening and which has significant potential for devising therapeutic treatments. Two previously unknown common structural mutations have been identified at codons 306 and 316 in the APOH gene which appear to be protective against the occurrence of SLE and antiphospholipid antibodies. While 8.3% of the general U.S. White population is a carrier of the codon 306 mutation, its frequency is only 1.8% in SLE patients. It has also been found according to the present invention that APOH from individuals who carry mutations at both codons (compound heterozygotes) does not bind to negatively charged phospholipids and thus these individuals may be precluded from producing APOH-dependent antiphospholipid antibodies which can lead to related thrombotic disorders.

The two structural mutations at codons 316 and 306 in the fifth domain of apoH render apoH unable to bind to negatively charged phospholipid, in particular, phophatidylserine ("PS"). The missense mutation at codon 316 (TGG→TCG) involves the substitution of Cys-306 by Gly-306 which causes the disruption of a disulfide bond between Cys-281 and Cys-306 and affects the normal configuration of the fifth domain of apoH that appears to be critical for clustering positively charged amino acids along with the four hydrophobic amino acids sequence. ApoH from the two homozygotes studied (Ser-316/Ser-316) and all seven compound heterozygotes (Ser-316/Gly-306) failed to bind to PS; all heterozygotes at one or the other sites and wild type showed normal PS binding. These data indicate that the fifth domain of apoH harbors the lipid binding region.

It is noteworthy that the lack of apoH binding to PS that is associated with the codons 306 and 316 mutations is confined to individuals who are APOH 3-3 homozygous on IEF-immunoblot gels, using polyclonal antiserum, and who also showed reactivity with monoclonal antibody ("mAb") 3D11. In the general Caucasian population of the United States the frequency of the APOH 3-3 phenotype is 1.66% (calculated in 661 individuals, see, Sanghera, D. K., et al., *Hum. Genet.* 100:57 (1997)), and most of them (1.36%) show reactivity with mAb 3D11 and are also carriers of the Ser-316 mutation. Of those with the APOH 3-3 phenotype, 0.91% are either compound heterozygous for the Ser-316/Gly-306 mutations or homozygous for the Ser-316 mutation and show no binding with lipid. If it is estimated that there are 220 million Caucasians in the United States, then 2 million (0.91%) people may be precluded from the production of apoH-dependent aPA and, thus, be protected from apoH-dependent thrombosis and related disorders.

223 SLE White women patients, and 288 U.S. Whites from the general population were also screened for the codon 306 mutation. It was found that compared to 8.3% (24 out of 288) individuals in the general population only 1.8% (4 out of 223) of SLE patients were carriers of the codon 306 mutation and this difference is statistically significant (P<0.001). These data strongly indicate that the codon 306 mutation provides protection against SLE and about 8% of the general U.S. White population (about 18 million people) are at extremely low risk of contracting SLE.

The present invention provides a means of identifying DNA sequences containing the mutation(s) for protection against SLE and the production of apoH-dependent antiphospholipid autoantibodies. Therefore, the invention additionally provides means for diagnosing the disease in patients, and identifying carriers of the genetic defect. This aspect of the invention includes methods for screening a potential SLE carrier or patient for the presence of an identified mutation and/or a different mutation in the APOH gene. It can be appreciated that the identification of the molecular basis of the APOH protein polymorphism helps to elucidate the structual-functual relationship of apoH in the production of antiphospholipid autoantibodies which can be used to design therapies. For example, a therapeutic agent can be designed which prevents apoH from binding to negatively charged phospholipid which prevents production of antophospholipid autoantibodies. Such a compound can be administered to patients in a variety of ways well known in the art.

Various aspects of the present invention require the use of primers which hybridize with nucleic acid sequences of the APOH gene. Commercial PCR amplification equipment and kits such as those from Perkin Elmer-Cetus are readily available. The present invention provides primer pairs (forward and reverse) for each of the eight APOH exons (see, Table 1 below). In particular, the primer pairs for exon 7 and exon 8 flank the mutation sites for codon 306 and codon 316, respectively. Exon 3 harbors the mutation site for codon 88 which is present in the APOH*1 allele and a suitable pair of amplification primers are provided by the present invention. In general, suitable primers will comprise, at a minimum, an oligomer at least about 20 nucleotides in length. Nucleic acid synthesizers (e.g., those of Applied Biosystems, Inc., Foster City, Calif.) and use thereof are well known in the art for manufacturing primers.

By use of the nucleotide sequences and DNA materials provided by the present invention, effective testing procedures are provided to identify carriers of mutations in apolipoprotein H which can protect against the individual's production of antiphospholipid autoantibodies and the associated thrombotic and fetal problems. Methods and DNA materials are also provided to detect a mutation in the APOH gene which can provide general protection against the occurrence of lupus.

There are many ways of carrying out conventional genetic screening assays known to the art. Several well known types of assays may be carried out using the oligonucleotides and DNA material of the present invention. In particular, the methods of the present invention can be advantageously carried out using genetic screening of biological samples using any of the following techniques:

Direct sequencing: The DNA from an individual being tested can be cloned by methods well known in the art. The cloned sequence can then be evaluated for mutations in its nucleic acid sequence by direct sequencing of the screened individual's APOH gene.

Polymerase Chain Reaction ("PCR"): This method can be used to test very small amounts of DNA obtained from an individual. DNA sequences in the region flanking the portion of the APOH gene known to contain a given mutation are amplified using oppositely oriented converging oligonucleotide primers. Sequencing or other analysis of the amplified sequences is thereby simplified. The mobility of heteroduplex PCR products in polyacrylamide gels indicates the presence or absence of a mutation in the APOH gene.

Restriction Fragment Length Polymorphism ("RFLP"): Restriction enzymes can be used which provide a characteristic pattern of restriction fragments, wherein a restriction site is either missing or an additional restriction site is introduced in the mutant allele. Thus, DNA from an individual and from control DNA sequences are isolated and subjected to cleavage by restriction enzymes which are known to provide restriction fragments which differentiate between mutant and normal alleles, and the restriction patterns are identified.

Single Strand Conformation Polymorphism ("SSCP"): This test is a rapid, sensitive assay for nucleotide alterations, including point mutations (see Orita, M., et al., *Genomics* 5: 874 (1989). DNA segments 100–400 bp in length are amplified by PCR, heat denatured, and electrophoresed on high resolution, non-denaturing acrylamide gels. Under these conditions, each single-stranded DNA fragment assumes a secondary structure determined in part by its nucleotide sequence. Single base changes can significantly affect the electrophoretic mobility of the PCR product.

In the above methods of screening (assays), either the presence of the normal or mutant APOH gene coding for the apoH polypeptide can be detected. Additionally, ELISA can be used to measure phospholipid binding by apoH. For the assays, kits are provided by the present invention to carry out the methods of the invention. These kits include oligonucleotide primers of the present invention that flank the regions of the APOH gene that contain point mutations of interest.

It will be appreciated by a skilled worker in the art that the identification of the genetic defect in a genetic disease, coupled with the provision of the DNA sequences of both normal and disease-causing alleles, provides the full scope of diagnostic and therapeutic aspects of such an invention as can be envisaged using current technology.

The following Examples are intended to illustrate but not limit the invention.

In the following example the structural mutations in the fifth domain of apoH are identified and those mutations are investigated for their affect on phospholipid binding.

EXAMPLE 1

Structural Mutations In apoH

Methods

Isoelectric Focusing (IEF)/Immunoblotting

Initial screening for the APOH protein polymorphism with polyclonal anti-apoH by IEF-immunoblotting was carried out as described originally by Kamboh, M. I., et al., *Am. J. Hum. Genet*. 42:452(1988) and modified for the mAb 3D11 as described by Kamboh, M. I., et al., *Hum. Genet* 95:385(1995). mAb 3D11 was a gift from Dr. John McIntyre, Methodist Hospital of Indiana, Indianapolis, Ind., and is available upon request. Briefly, plasma samples were applied in 5% polyacrylamide gel (6 M urea) in a pH range of 4.5–5.8. IEF was carried out at 10 W, 2000 V and 250 mA for 3 hours followed by protein transfer onto a nitrocellulose membrane. Membranes were incubated first with a primary antibody (polyclonal rabbit antihuman apoH or monoclonal mouse antihuman 3D11) (Biotechnology Research Institute, Rockville, Md.) and then with a secondary antibody IgG conjugated with alkaline phosphatase (Incstar Corp., Stillwater, Minn.) Finally, the membranes were histochemically stained for alkaline phosphates to visualize apoH bands.

PCR and DNA Sequencing

DNA samples from individuals with known protein typings were subjected to PCR to amplify the entire coding sequence of the fifth domain of the APOH gene using a forward primer ("APOH 2") in the 5' flanking intron, 5'-GTGTAGGTGTACTCATCTACTGTG-3' (SEQ ID NO: 1) as described by Steinkasser, A., et al., *Hum. Genet*. 91:401 (1993) and a reverse primer ("APOH 5") in the non-coding 3' flanking region, 5'-TGGATGAACAAGAAACAAGTG-3' (SEQ ID NO: 2). DNA sequencing from both directions identified an intron (termed "intron 7") and intron-exon boundaries corresponding to exons 7 and 8. Subsequently, exon 7 was amplified using APOH 2 (forward primer) in conjunction with APOH 9 (reverse primer), 5'-CAAGTGGGAGTCCTAGCTAA-3' (SEQ ID NO: 3) Similarly, exon 8 was amplified using APOH 10 (forward primer), 5'-TTGTTCCCTTAGAATGTTTAT-3' (SEQ ID NO: 4) in conjunction with APOH 5 (reverse primer). 1 µg of genomic DNA from EDTA anticoagulated blood samples was subjected to PCR amplification using forward and reverse primers specific for each exon in 50 µl of reaction mixture containing 0.3 µM of each of the primers, 200 µM of each dNTP (LKB Pharmacia, Piscataway, N.J.); 5 µl of 10×reaction buffer (100 mM Tris HCl (pH 9.0), 500 mm KCl, and 1% Triton X-100, pH 9.0); 3.5% DMSO and 1.25 units of Taq DNA polymerase (Life Technologies, Grand Island, N.Y.). After initial denaturing of the DNA for 5 minutes at 95° C., the reaction mixture was subjected to 30 cycles of denaturation for 1 minute at 95° C., 1.5 minute of annealing at 57° C. (for exons 7 and 3) and at 49° C. (for exon 8), and 2 minutes of extension at 72° C. DNA sequencing of purified PCR product was carried out directly on double-stranded DNA by the dideoxynucleotide chain termination method using a PCR Product Sequencing Kit and sequence version 2.0 (U.S. Biochemicals, Cleveland, Ohio) with $^{35}$S-labeled dATP (DuPont, Wilmington, Del.). Sequenced products of all fragments were migrated on 6% denaturing (7M urea) glycerol-tolerant sequencing gel (U.S. Biochemicals). Vacuum dried gels were autoradiographed on Kodak X-ray film for 24 hours.

DNA Polymorphisms

Population screenings of two newly identified mutations in exon 7 (codon 306) and exon 8 (codon 316) were carried out by restriction enzyme digestion of PCR products with CviJI (Molecular Biology Resources, Milwauki, Wis.) and BstBI (New England Biolabs, Beverly, Mass.) enzymes, respectively, followed by electrophoresis on either 9% polyacrylamide (codon 306 mutation) or 2% Nusieve agarose (codon 316 mutation) gels. A mutation in exon 3 (codon 88) was carried out by restriction enzyme digestion of PCR products with Tsp509I (New England Biolabs) followed by electrophoresis on 2% Nusieve agarose gel.

Phospholipid Binding of apoH by ELISA

Phospholipid binding by apoH was measured by ELISA according to the method of Wagenknecht, D. R., et al., *Thromb. Haemost*. 69:361 (1993). Briefly, flat-bottom Titertek microtiter plates (ICN, Horsham, Pa.) were coated with 30 µl of a 50 µg/ml solution of cardiolipin or PS (Sigma, St. Louis, Mo.) diluted in methanol:chloroform (3:1) and they were dried under a stream of nitrogen. The plates were given three 2-minute washes with TRIS-buffered NaCl (TBS; 0.02 M TRIS, 0.15 M NaCl, pH 7.3) after antigen coating, blocking, sera, antibody and conjugate incubations as are well known in the art. The plates were blocked with 10% bovine serum albumin ("BSA") (Sigma). Each serum was diluted (1:80 in 1% BSA/TBS), and incubated in triplicate wells (50 µl/well) for 60 minutes. 50 µl of mAb 3G9 (a gift from Dr. John McIntyre, Methodist Hospital of Indiana, and available upon request) (0.5 µg/ml) was then incubated in each well for 30 minutes followed by a 30-minute incubation with an alkaline phosphate conjugated rabbit antimouse IgG (Incstar). Development substrate (paranitrophenylphosphate tablets in 10% w/v diethanolamine, 5 mM $MgCl_2$, pH 9.8) was added to each well (50 µl), and the plates were incubated in the dark at 37° C. for 45 minutes. Color development was stopped by the addition of 75 µl of 3 M NaOH, then the optical density of each well was measured at 405 nm.

Results/Discussion

Molecular Basis of the APOH*3$^w$, Allele

DNA samples from two individuals carrying the APOH*3$^w$ allele were used to amplify the coding region of the entire fifth domain of apoH (amino acids 243–326) by PCR. The observed PCR product was more than twice the expected size of the 401 bp fragment, which indicated the presence of an intron. Direct DNA sequencing from both directions identified an intron which interrupted the codon 309 sequence, which confirms that the fifth domain of apoH is encoded by the last two exons, 7 and 8 (data not shown). Subsequently, new reverse (APOH 9) and forward (APOH 10) PCR primers were designed in intron 7 to amplify the exons 7 and 8, respectively in combination with originally designed PCR primers (APOH 2, APOH 5) for the fifth domain sequence. A point mutation was identified at the second position of codon 316 in exon 8 (TGG→TCG) which replaced Trp-316 by Ser-316 as shown in FIG. 1A. This point mutation creates a restriction site for the BstBI enzyme and, therefore, a PCR-based restriction analysis was performed to screen the remaining individuals who were carriers of the APOH*3 allele. The uncut fragment size of 148 bp corresponded to the Trp-316 wild type and the 86 bp fragment and the 62 bp fragment corresponded to the Ser-316 mutant type as shown in FIG. 1B. All samples which reacted with mAb 3D11 (APOH*$3^w$ allele) had the Ser-316 mutation and none of the mAb 3D11 negative samples had this mutation, strongly confirming that a missense mutation at codon 316 is responsible for the APOH*$3^w$ reactivity with mAb 3D11. Only 2 of the 12 samples which showed reactivity with mAb 3D11 and which were originally classified as APOH 3-3 by polyclonal antibody, were homozygous for the Ser-316 mutation. The remaining samples were heterozygous having both the wild and mutant types (Trp/Ser). Direct DNA sequencing of the remaining 7 APOH exons from an individual homozygous for the Ser-316 allele did not identify any other mutations (data not shown).

Effect of the Codon 316 Mutation on Lipid Binding

Figure 2:
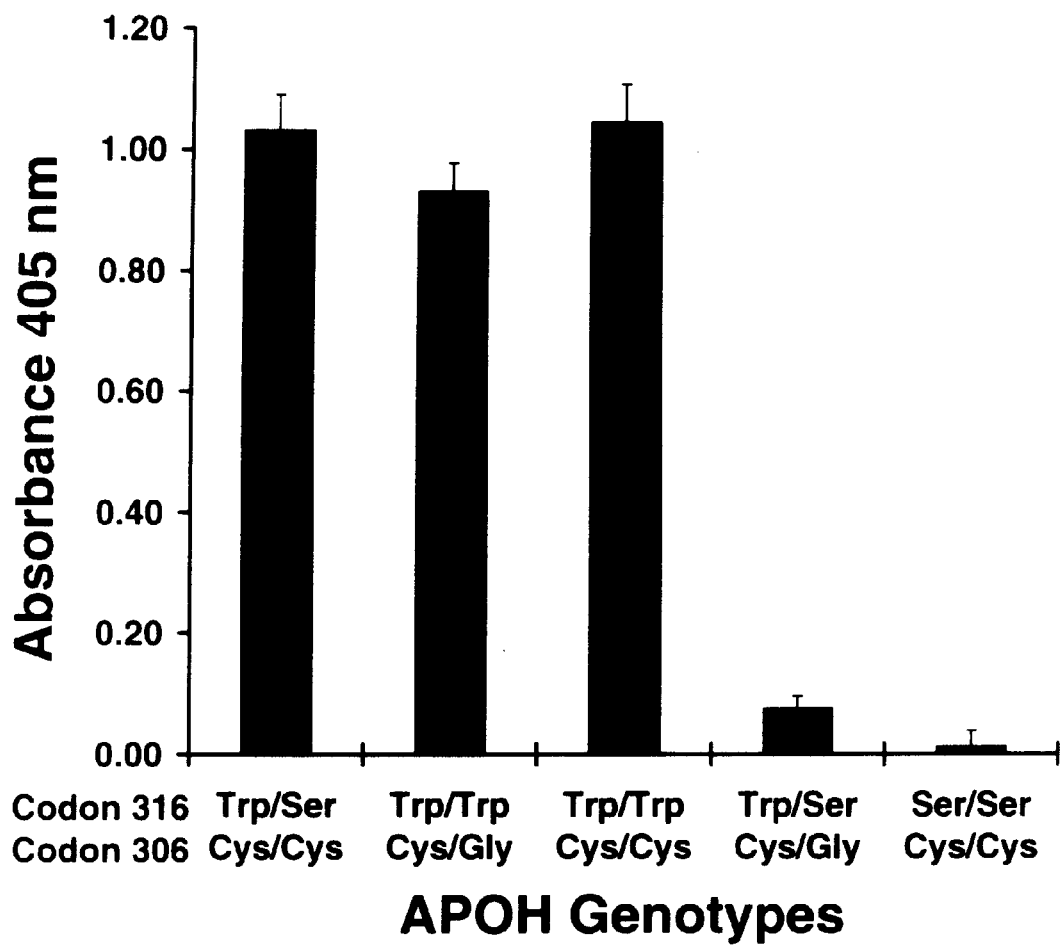
FIG. 2 is a graph showing phosphatidylserine ("PS") binding by apoH with mutations at codons 316 and 306. The mean and standard deviations of ELISA $OD_{405}$ values of serum apoH binding to PS are illustrated among different APOH genotypes. The apoH from individuals who are heterozygous at codon 316 (Trp/Ser, Cys/Cys; n=8) or codon 306 (Trp/Trp, Cys/Gly; n=19) bound to PS-coated ELISA plates as well as the apoH from individuals having wild types at both codons (Trp/Trp, Cys/Cys; n=4). In contrast, apoH from individuals homozygous for the codon 316 mutation (Ser/Ser, n=2) or from compound heterozygotes (Trp/Ser, Cys/Gly; n=7) did not bind to PS.
Figures 3A, 3B:
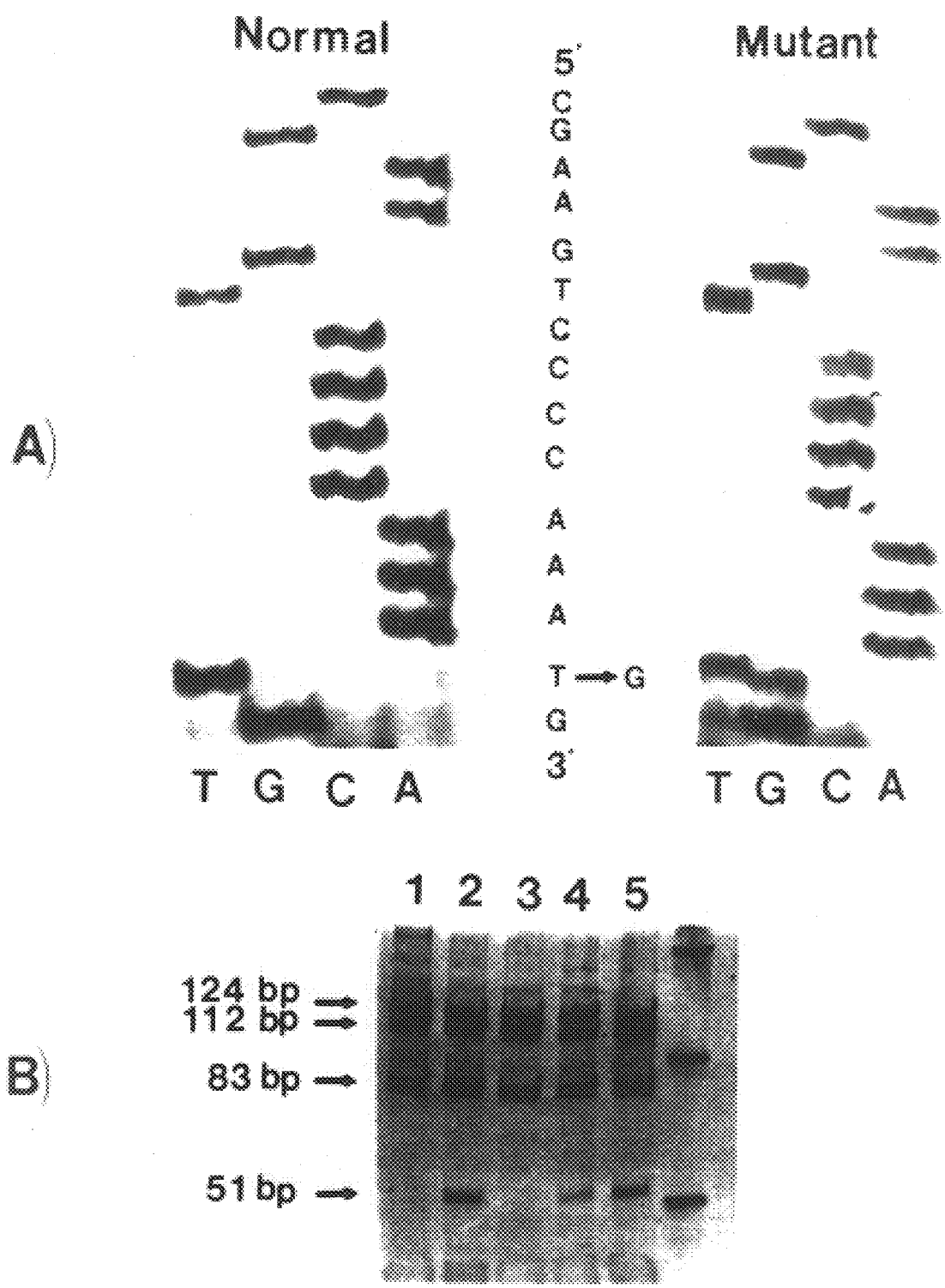
FIGS. 3A and 3B are photographs showing identification of a point mutation at codon 306 (TGC→GGC) by direct DNA sequencing of double stranded DNA (FIG. 3A), and by restriction analysis with CviJI (FIG. 3B).

Since mAb 3G9 recognized the products of all APOH alleles in a previous study (Kamboh, M. I., et al., *Hum Genet*. 95:385 1995)), 3G9 was used to detect PS binding by apoH in the ELISA. The two individuals homozygous for the Ser-316 mutation showed no binding with PS as seen in FIG. 2 but apoH binding to PS was detected in 8 individuals who were heterozygous for this mutation as seen in FIG. 2, indicating that homozygosity of the Ser-316 mutation is essential to negate lipid binding. However, apoH from 7 additional individuals who were heterozygous for the Ser-316 mutation also showed no PS binding as also shown in FIG. 2 which suggests that the presence of an additional mutation(s) is required to interact with the Ser-316 mutation in its heterozygous form to negate PS binding.

Identification of Codon 306 Mutation and its Role in Lipid Binding

Figures 4A, 4B, 4C:
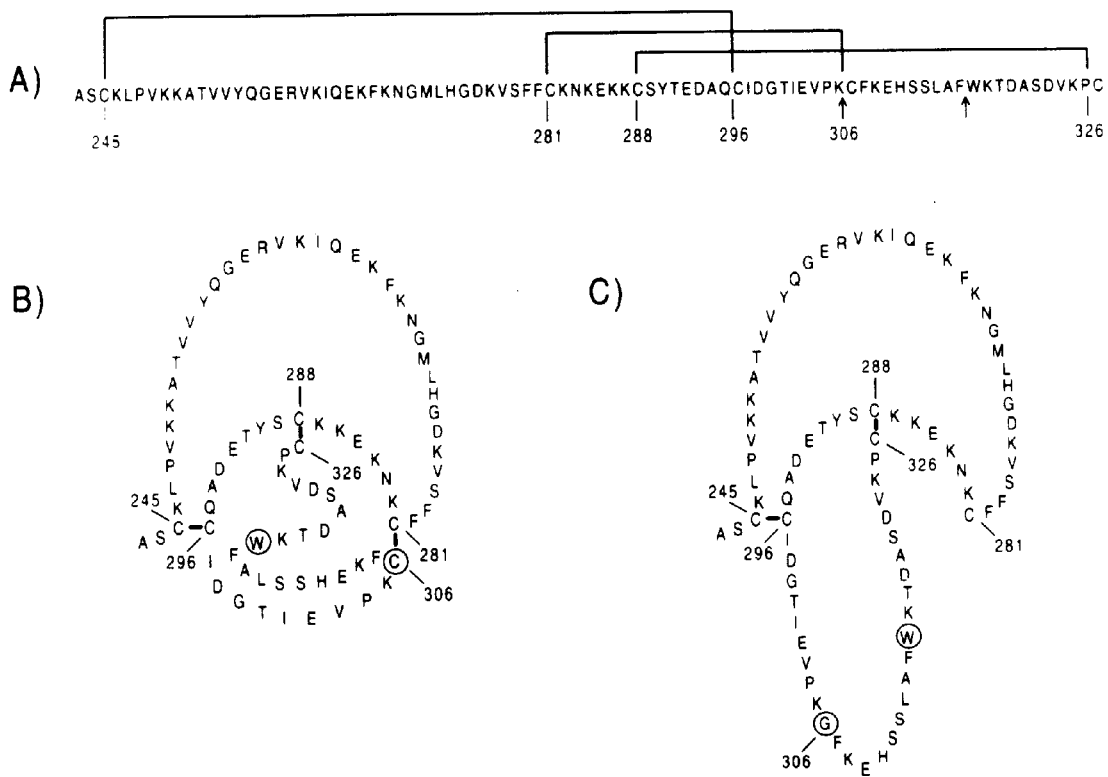
FIGS. 4A–4C illustrate the fifth domain of human apoH.

DNA from one of the 7 heterozygotes with the Ser-316 mutation which revealed no apoH binding with PS was subjected to sequencing to identify the second putative functional mutation. A missense mutation at codon 306 (TGC→GGC) was found in exon 7 which replaced Cys-306 by Gly-306 (FIG. 3A). This point mutation also created a restriction site for the CviJI enzyme and, therefore, a PCR based screening method was devised to screen all the remaining individuals who were heterozygous for the Ser-316 mutation (FIG. 3B). While none of the 8 heterozygotes for the Ser-316 mutation, who showed PS binding, had the Gly-306 mutation, all 7 heterozygotes with the Ser-316 mutation, who showed no PS binding, had the Gly-306 mutation (FIG. 2). These data show that the 7 individuals with the Ser-316 and Gly-306 mutations are compound heterozygotes. To determine if the Gly-306 mutation is widely distributed in the general population or is present only in combination with the Ser-316 mutation, 331 DNA samples were examined. It was found that the Gly-306 mutation was present in approximately 8% of the general U.S. Caucasian population irrespective of the presence or absence of the Ser-316 mutation. Altogether 19 individuals were identified who were heterozygous for the Gly-306 mutation and did not carry the Ser-316 mutation; apoH from all of these 19 samples showed binding to PS (FIG. 2), thereby suggesting that one copy of this mutation is not sufficient to prevent apoH binding to PS. No individual homozygous for the Gly-306 mutation was observed in this investigation. This is however not a surprising observation because the expected frequency of the Gly-306/Gly-306 homozygous in the 331 samples examined is only 0.5 or 0.15%.

Consequence of Codons 306 and 316 Mutations on Lipid Binding

The fifth domain apoH consists of 6 Cys residues and the resulting 3 disulfide bonds have been mapped (see, Steinkasserer, A., et al., *FEBS Lett*. 313:192 (1992)) to show linkage between Cys-245 to Cys-296, Cys-281 to Cys-306 and Cys-288 to Cys-326 as seen in FIG. 4A. The formation of the disulfide bonds between Cys-281 to Cys-306 brings five additional positively charged amino acids (4 Lys, 1 His) at positions 305, 308, 310, 317 and 324 to the highly positive charged sequence of Lys-Asn-Lys-Glu-Lys-Lys at positions 282–287. (FIG. 4B) This model clusters 9 positively charged amino acids (8 Lys at positions 282, 284, 286, 287, 305, 308, 317 and 324 positions and 1 His at position 310) in the fifth domain and makes it the most plausible configuration for binding with negatively charged phospholipids. In addition to the negatively charged amino acids in this loop, there is a hydrophobic sequence at positions 313–316 (Leu, Ala, Phe, Trp) in this loop and that may serve as an interaction site with the fatty acid chains of the phospholipid aggregate. Id. The substitution of Trp-316 by Ser-316 appears to affect the hydrophobic bonding between apoH and PS. On the other hand, the substitution of Cys-306 by Gly-306 would result in the breakage of the second disulfide bond between Cys-281 to Cys-306 and will disrupt the normal configuration of the inner loop as seen in FIG. 4C which appears to be necessary to cluster positively charged amino acids along with the four hydrophobic amino acids at positions 313–316.

An additional missense mutation (G→A) was identified in exon 3 in the APOH*1 allele which was detected by protein methods as described further below.

This study was undertaken to identify unique structural mutations in the APOH gene which affect the binding of apoH to anionic phospholipids. Functional mutations, in the fifth domain of APOH were focused on for ionic interaction with anionic phospholipids. Two naturally occurring structural mutations at codons 306 and 316 in the fifth domain were identified which appear to be functionally related with the apoH ability to bind lipid. Both mutations reside in the C-terminal of apoH only 9 amino acids apart. The mutation at codon 316 involves the substitution of one of the four hydrophobic amino acids at position 313–316 (Leu, Ala, Phe, Trp) which are highly conserved in primates including bovine, rat, mouse, dog and human (references given above). This hydrophobic sequence is suggested to be involved in hydrophobic bonding with the fatty acid chains of the anionic phospholipid aggregate. The present data indicate that the integrity of this hydrophobic sequence is critical for binding to anionic phospholipids because serum apoH from two individuals who were homozygous for the Ser-316 mutation did not bind to PS (see FIG. 2). It appears that the homozygosity of the Ser-316 mutation is necessary to prevent apoH binding to anionic phospholipids because individuals heterozygous for this mutation showed complete lipid binding (FIG. 2). However, when the Ser-316 mutation occurs in conjunction with the Gly-306 mutation it also prevents the binding of apoH to PS (FIG. 2). Taken together, these data suggest that these mutations operate in a recessive fashion where both chromosomes must carry either the same mutation at one site (homozygous for the Ser-316 mutation) or different mutations at two different sites (compound heterozygous for the Ser-316 and Gly-306 mutations). Although no example of the Gly 306/Gly-306 was observed in this investigation, it can be predicted that apoh from such homozygous individuals will not bind to anionic phospholipids.

The Gly-306 mutation does not seem to have direct impact on protein-lipid interaction because this does not involve any charged amino acid. However, the substitution of Cys-306 by Gly-306 disrupts the critical disulfide bond which seems important in clustering several positively charged amino acids (see FIGS. 4B and 4C). By molecular modeling of the fifth GP-1 domain and highlighting the lysine residues Steinkasserer, A., et al., FEBS Lett. 313 192 (1992) have shown that lysine at positions 282, 284, 286, 287 and 324 may form a lipid binding region since in the model they were clustered at the distal end. The disruption of the disulfide bond between Cys-306 and Cys-281 would effect the positioning of Lys-324 and also move Lys-308, Lys-305 and His-310 away from the positively charged cluster along with the four hydrophobic amino acids sequence at positions 313–316 (see FIG. 4C). Recent findings that a clipped apoH molecule, which was cleaved between Lys-317 and Thr-318, failed to bind to cardiolipin and lost its cofactor activity (Hunt, J. E., et al., Proc. Natl. Acad. Sci. USA 90: 2141 (1993)) and a synthetic peptide containing Cys287-Cys288 sequence inhibited the binding of apoH to cardiolipin (Hunt, J. E. et al., J. Immunol. 152: 653 (1994)) provide further evidence that the proposed configuration of the fifth domain is essential for lipid binding and structural changes in this region, as shown here by the Gly-306 and Trp-316 mutations, would affect the normal configuration of apoH (FIG. 4).

Notably, the lack of apoH binding to PS associated with the codons 306 and 316 mutations is confined to individuals who are APOH 3-3 homozygous on IEF-immunoblot gels, using polyclonal antiserum, and also showed reactivity with mAb 3D11. In the general Caucasian population of the United States the frequency of the APOH 3-3 phenotype is 1.66% (calculated in 661 individuals (Sanghera, D. K., et al., Hum. Genet. 100:57 (1997)), and most of them (1.36%) show reactivity with mAb 3D11 and are also carriers of the Ser-316 mutation. Of those with the APOH 3-3 phenotype, 0.91% are either compound heterozygous for the Ser-316/Gly-306 mutations or homozygous for the Ser-316 mutation and show no binding with lipid (see FIG. 2). If it is assumed that there are 220 million Caucasians in the United States then 2 million (0.91%) may be precluded from the production of apoH-dependent aPA and, thus, be protected from apoH-dependent thrombosis and related disorders.

EXAMPLE 2 apoH Polymorphism/Identification of Codon 88 Mutation

To determine the molecular basis of the APOH*1 allele, DNA samples from known APOH*1 alleles were PCR-amplified and subjected to direct DNA sequencing of all APOH coding exons as described above in Example 1 using primers as listed in Table 1 below.

TABLE 1

Summary of primer sequences used to PCR amplify various apolipoprotein H gene (APOH) exons and size of each amplified fragment.

| Exon | Primer | | | Primer sequence (5'-3') | Fragment size (bp) |
|---|---|---|---|---|---|
| Exon 1 | Upstream | (APOH SigF) | (SEQ ID NO:5) | CCA CTT TGG TAG TGC CAG TGT GAC | 156 |
| | Downstream | (APOH SigR) | (SEQ ID NO:6) | TGA CAT ATA CGA AGG GGT TGG AT | |
| Exon 2 | Upstream | (APOH 2F) | (SEQ ID NO:7) | ACT TTA AAA TGC AAA TAG AGA TTT G | 307 |
| | Downstream | (APOH 2R) | (SEQ ID NO:8) | GAC GAG GTA GCT TAT TCC TCC A | |
| Exon 3 | Upstream | (APOH 3F) | (SEQ ID NO:9) | GAA ATT TAC CTG TTT ATG TTT | 207 |
| | Downstream | (APOH 3R) | (SEQ ID NO:10) | TGT GCT CAG TCT GTT AAC TG | |
| Exon 4 | Upstream | (APOH 4F) | (SEQ ID NO:11) | TGG AGA GAT ATT TGA GAT GTC | 208 |
| | Downstream | (APOH 4R) | (SEQ ID NO:12) | TAG TGC TAA AAC CAG AAA GGT | |
| Exon 5 | Upstream | (APOH 5F) | (SEQ ID NO:13) | ATC ATC TGC CCT CCA CCA TCC A | 186 |
| | Downstream | (APOH 5R) | (SEQ ID NO:14) | GCA TTC TGG TAA TTT AGT CCA A | |
| Exon 6 | Upstream | (APOH 7F) | (SEQ ID NO:15) | ATT GGA TAG CAC TAT TTA TTA | 296 |
| | Downstream | (APOH 7R) | (SEQ ID NO:16) | ATC AAT TCA GAG TCT TAC AG | |
| Exon 7 | Upstream | (APOH 2) | (SEQ ID NO:1) | GTG TAG GTG TAC TCA TCT ACT GTG | 337 |
| | Downstream | (APOH 9) | (SEQ ID NO:3) | CAA GTG GGA GTC CTA GCT AA | |
| Exon 8 | Upstream | (APOH 10) | (SEQ ID NO:4) | TTG TTC CCT TAG AAT GTT TAT | 148 |
| | Downstream | (APOH 5) | (SEQ ID NO:22) | TGG ATG AAC AAG AAA CAA GTG | |

Figures 5A, 5B:
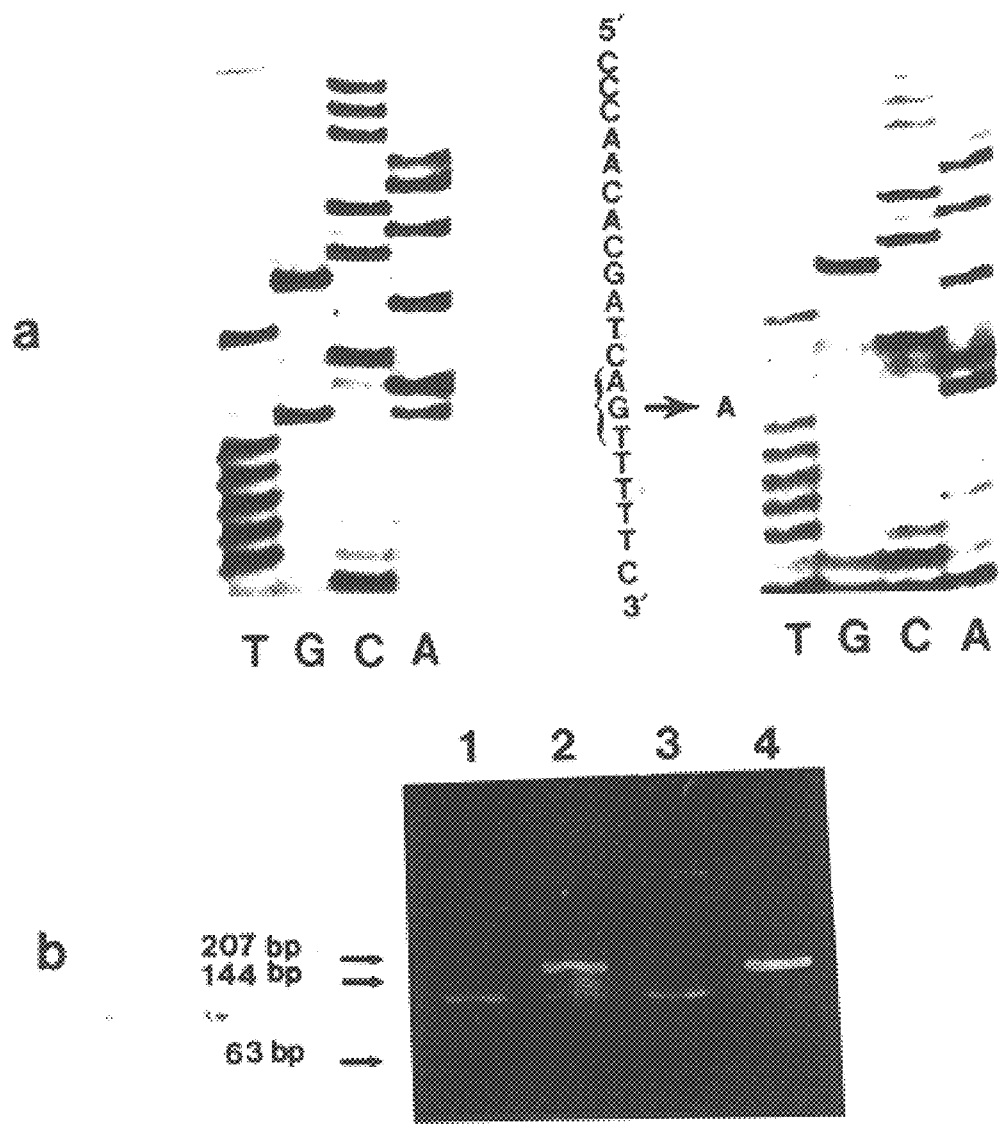
FIGS. 5A and 5B are photographs showing identification of a point mutation at codon 88 (AGT→AAT) of exon 3, which corresponds to the APOH*1 allele.

Compared with the wild-type sequence of APOH*2 (Mehdi, H., et al., Gene 108:293 (1991); Kristensen, T., et al., FEBS Lett 289:183 (1991); and Steinkasseror, A., et al., Biochem. J. 277:387(1991)), one missense mutation was identified in exon 3. The exon 3 missense mutation (G→A) altered amino acid residue from Ser to Asn at codon 88 as seen in FIG. 5A and corresponded to the APOH*1 allele. This substitution also created a restriction site for Tsp509I, and, therefore, all the remaining APOH*1 carriers were screened by restriction analysis to confirm the correlation between the protein and DNA polymorphisms. Restriction fragment patterns of three possible genotypes after digestion with Tsp509I are shown in FIG. 5B. Genetic screening of all APOH*1 carriers (76 Non-Hispanic Whites ("NHW"), 38 Hispanics and 9 blacks; see also Table 1) and an equal number of non-APOH*1 carriers confirmed that the G→A substitution was specific for the APOH*1 allele, identified on IEF. The frequency of the Asp-88 allele in NHWs, Hispanics and blacks was 0.059, 0.043, and 0.011, respectively.

Although the invention has been described in detail for the purposes of illustration, it is to be understood that such detail is solely for that purpose and that variations can be made therein by those skilled in the art without departing from the spirit and scope of the invention except as it may be limited by the claims.

We claim:

1. A method to determine the presence or absence of a missense mutation at codon 306 of exon 7 of the apolipoprotein H gene in an individual wherein said missense mutation protects said individual against the occurrence of systemic lupus erythematosus, comprising the steps of:
   a) obtaining genomic DNA from said individual;
   b) amplifying said genomic DNA with a primer pair for exon 7 of the apolipoprotein H gene; and
   c) determining the presence or absence of a missense mutation at codon 306 of exon 7 of the apolipoprotein H gene from the codon TGC to GGC.

2. The method of claim 1, wherein said genomic DNA is prepared from a sample of blood from said individual.

3. The method of claim 1, wherein said primer pair for exon 7 of the apolipoprotein H gene comprises APOH 2, 5'-GTGTAGGTGTACTCATCTACTGTG-3' (SEQ ID NO: 1) and APOH 9, 5'-CAAGTGGGAGTCCTAGCTAA-3' (SEQ ID NO: 3).

4. The method of claim 1 wherein said mutation is detected by DNA sequencing of the amplified genomic DNA from said sample.

5. The method of claim 1, wherein said mutation is detected by restriction analysis.

6. The method of claim 1, wherein said mutation is detected by restriction fragment length polymorphism analysis.

7. A method to determine the presence or absence of missense mutations in the fifth domain apolipoprotein H gene at codon 306 (TGC→GGC) and codon 316 (TGG→TCG) of an individual that render apolipoprotein H protein unable to bind to negatively charged phospholipid, comprising the steps of:
   a) obtaining genomic DNA from said individual;
   b) amplifying said genomic DNA with a primer pair for exon 7 for codon 306;
   c) amplifying said genomic DNA with a primer pair for exon 8 for codon 316; and
   d) determining the presence or absence of said mutations at codon 306 of exon 7 and codon 316 of exon 8 in the fifth domain of said apolipoprotein H gene.

8. The method of claim 7, wherein said genomic DNA is prepared from a sample of blood.

9. The method of claim 7, wherein said negatively charged phospholipid is phosphatidylserine.

10. The method of claim 7, wherein said primer pair for amplification of exon 7 comprises APOH 2, 5'-GTGTAGGTGTACTCATCTACTGTG-3' (SEQ ID NO: 1), and APOH 9, 5'-CAAGTGGGAGTCCTAGCTAA-3' (SEQ ID NO: 3).

11. The method of claim 7, wherein said primer pair for amplification of exon 8 comprises APOH 10, 5'-TTGTTCCCTTAGAATGTTTAT-3' (SEQ ID NO: 4) and APOH 5, 5'-TGGATGAACAAGAAACAAGTG-3' (SEQ ID NO: 2).

12. The method of claim 7, wherein said mutations are detected by DNA sequencing of the amplified genomic DNA from said sample.

13. The method of claim 7, wherein said mutations are detected by restriction analysis.

14. The method of claim 7, wherein said mutations are detected by restriction fragment length polymorphism analysis.

15. A method to determine the likelihood of an individual producing antiphospholipid autoantibodies and subsequently becoming afflicted with related thrombotic disorders comprising:
   a) obtaining a sample of genomic DNA from said individual; and
   b) detecting the presence or absence of missense mutations in the fifth domain of apolipoprotein H gene from said individual that preclude apolipoprotein H protein from binding to negatively charged phospholipid wherein the presence of said missense mutations is indicative of a decrreased likelihood of the the individual producing antiphospholipid autoantibodies.

16. The method of claim 15, wherein said mutations in the fifth domain of dain apolipoprotein gene comprisse mutations of codon 306 and codon 316.

17. The method of claim 16, wherein said mutations are detected by:
   a) amplifying the regions of the apolipoprotein H gene contained in said genomic DNA that flank the positions of said missense mutations in said apolipoprotein H gene; and
   b) determining the presence or absence of said mutations in the amplified DNA.

18. The method of claim 17, wherein said amplification is carried out using primer pair APOH 2 (SEQ ID NO: 1) and APOH 9 (SEQ ID NO: 3) for codon 306 and primer pair APOH 10 (SEQ ID NO: 4) and APOH 5 (SEQ ID NO: 2) for codon 316.

19. A method of determining the likelihood of an individual being protected against the occurrence of systemic lupus erythematosus, comprising:
   a) obtaining a sample of genomic DNA from said individual; and
   b) detecting the presence or absence of a missense mutation at codon 306 in the fifth domain of apolipoprotein H which causes the substitution Cys-306 by Gly-306 whereby the presence of said missense mutation indicates the likelihood of said individual being protected against the occurrence of systemic lupus erythematosus.

20. The method of claim 19, wherein said genomic DNA is prepared from a sample of blood from said individual.

21. The method of claim 19, wherein said detection of a missense mutation comprises amplifying said genomic DNA with a primer pair for amplification of exon 7 of the apoliprotein H gene.

22. The method of claim 21, wherein said primer pair for exon 7 of the apolipoprotein H gene comprises APOH 2, 5'-GTGTAGGTGTACTCATCTACTGTG-3' (SEQ ID NO: 1) and APOH 9, 5'-CAAGTGGGAGTCCTAGCTAA-3' (SEQ ID NO: 3).

23. The method of claim 19 wherein said point mutation is detected by DNA sequencing of the amplified genomic DNA from said sample.

24. The method of claim 19 wherein said missense mutation is detected by restriction analysis.

25. The method of claim 19 wherein said missense mutation is detected by restriction fragment length polymorphism analysis.

26. A kit for detection of the presence or absence of mutations in the human apolipoprotein H gene in an individual at codons 306 and 316, comprising:

at least one pair of amplification primers for amplification of each of said mutations, wherein said amplification primers for codon 306 comprise APOH 2, 5'-GTGTAGGTGTACTCATCTACTGTG-3' (SEQ ID NO: 1), and APOH 9, 5'-CAAGTGGGAGTCCTAGCTAA-3' (SEQ ID NO: 3), and said amplification primers for codon 316 comprise APOH 10, 5'-TTGTTCCCTTAGAATGTTTAT-3' (SEQ ID NO: 4), and APOH 5, 5'-TGGATGAACAAGAAACAAGTG-3' (SEQ ID NO: 2).

* * * * *

SEQUENCE LISTING (1) GENERAL INFORMATION:

(iii) NUMBER OF SEQUENCES:  16

(2) INFORMATION FOR SEQ ID NO:1:

(i) SEQUENCE CHARACTERISTICS:
        (A) LENGTH:        24 nucleotides
        (B) TYPE:          nucleic acid
        (C) STRANDEDNESS:  single
        (D) TOPOLOGY:      linear (ii) MOLECULE TYPE:    synthetic DNA (iii) SEQUENCE DESCRIPTION:  SEQ ID NO: 1:

GTGTAGGTGT ACTCATCTAC TGTG                                                24

(2) INFORMATION FOR SEQ ID NO:2:

(i) SEQUENCE CHARACTERISTICS:
        (A) LENGTH:        21 nucleotides
        (B) TYPE:          nucleic acid
        (C) STRANDEDNESS:  single
        (D) TOPOLOGY:      linear (ii) MOLECULE TYPE:    synthetic DNA (iii) SEQUENCE DESCRIPTION:   SEQ ID NO: 2:

TGGATGAACA AGAAACAAGT G                                                   21

(2) INFORMATION FOR SEQ ID NO:3:

(i) SEQUENCE CHARACTERISTICS:
        (A) LENGTH:        20 nucleotides
        (B) TYPE:          nucleic acid
        (C) STRANDEDNESS:  single
        (D) TOPOLOGY:      linear (ii) MOLECULE TYPE:    synthetic DNA (iii) SEQUENCE DESCRIPTION:   SEQ ID NO: 3:

CAAGTGGGAG TCCTAGCTAA                                                     20

(2) INFORMATION FOR SEQ ID NO:4:

(i) SEQUENCE CHARACTERISTICS:
        (A) LENGTH:        21 nucleotides
        (B) TYPE:          nucleic acid
        (C) STRANDEDNESS:  single
        (C) TOPOLOGY:      linear (ii) MOLECULE TYPE:    synthetic DNA (iii) SEQUENCE DESCRIPTION:   SEQ ID NO: 4:

TTGTTCCCTT AGAATGTTTA T                                                   21

(2) INFORMATION FOR SEQ ID NO:5:

(i) SEQUENCE CHARACTERISTICS:
        (A) LENGTH:        24 nucleotides
        (B) TYPE:          nucleic acid
        (C) STRANDEDNESS:  single
        (C) TOPOLOGY:      linear (ii) MOLECULE TYPE:    synthetic DNA (iii) SEQUENCE DESCRIPTION:   SEQ ID NO: 5:

-continued

```
CCACTTTGGT AGTGCCAGTG TGAC                                              24

(2) INFORMATION FOR SEQ ID NO:6:

(i) SEQUENCE CHARACTERISTICS:
        (A) LENGTH:       23 nucleotides
        (B) TYPE:         nucleic acid
        (C) STRANDEDNESS: single
        (C) TOPOLOGY:     linear (ii) MOLECULE TYPE:    synthetic DNA (iii) SEQUENCE DESCRIPTION:    SEQ ID NO: 6:

TGACATATAC GAAGGGGTTG GAT                                               23

(2) INFORMATION FOR SEQ ID NO:7:

(i) SEQUENCE CHARACTERISTICS:
        (A) LENGTH:       25 nucleotides
        (B) TYPE:         nucleic acid
        (C) STRANDEDNESS: single
        (C) TOPOLOGY:     linear (ii) MOLECULE TYPE:    synthetic DNA (iii) SEQUENCE DESCRIPTION:    SEQ ID NO: 7:

ACTTTAAAAT GCAAATAGAG ATTTG                                             25

(2) INFORMATION FOR SEQ ID NO:8:

(i) SEQUENCE CHARACTERISTICS:
        (A) LENGTH:       22 nucleotides
        (B) TYPE:         nucleic acid
        (C) STRANDEDNESS: single
        (C) TOPOLOGY:     linear (ii) MOLECULE TYPE:    synthetic DNA (iii) SEQUENCE DESCRIPTION:    SEQ ID NO: 8:

GACGAGGTAG CTTATTCCTC CA                                                22

(2) INFORMATION FOR SEQ ID NO:9:

(i) SEQUENCE CHARACTERISTICS:
        (A) LENGTH:       21 nucleotides
        (B) TYPE:         nucleic acid
        (C) STRANDEDNESS: single
        (C) TOPOLOGY:     linear (ii) MOLECULE TYPE:    synthetic DNA (iii) SEQUENCE DESCRIPTION:    SEQ ID NO: 9:

GAAATTTACC TGTTTATGTT T                                                 21

(2) INFORMATION FOR SEQ ID NO:10:

(i) SEQUENCE CHARACTERISTICS:
        (A) LENGTH:       20 nucleotides
        (B) TYPE:         nucleic acid
        (C) STRANDEDNESS: single
        (C) TOPOLOGY:     linear (ii) MOLECULE TYPE:    synthetic DNA (iii) SEQUENCE DESCRIPTION:    SEQ ID NO: 10:

TGTGCTCAGT CTGTTAACTG                                                   20
```

```
(2) INFORMATION FOR SEQ ID NO:11:

(i) SEQUENCE CHARACTERISTICS:
        (A) LENGTH:       21 nucleotides
        (B) TYPE:         nucleic acid
        (C) STRANDEDNESS: single
        (C) TOPOLOGY:     linear (ii) MOLECULE TYPE:    synthetic DNA (iii) SEQUENCE DESCRIPTION:    SEQ ID NO: 11:

TGGAGAGATA TTTGAGATGT C                                              21

(2) INFORMATION FOR SEQ ID NO:12:

(i) SEQUENCE CHARACTERISTICS:
        (A) LENGTH:       21 nucleotides
        (B) TYPE:         nucleic acid
        (C) STRANDEDNESS: single
        (C) TOPOLOGY:     linear (ii) MOLECULE TYPE:    synthetic DNA (iii) SEQUENCE DESCRIPTION:    SEQ ID NO: 12:

TAGTGCTAAA ACCAGAAAGG T                                              21

(2) INFORMATION FOR SEQ ID NO:13:

(i) SEQUENCE CHARACTERISTICS:
        (A) LENGTH:       22 nucleotides
        (B) TYPE:         nucleic acid
        (C) STRANDEDNESS: single
        (C) TOPOLOGY:     linear (ii) MOLECULE TYPE:    synthetic DNA (iii) SEQUENCE DESCRIPTION:    SEQ ID NO: 13:

ATCATCTGCC CTCCACCATC CA                                             22

(2) INFORMATION FOR SEQ ID NO:14:

(i) SEQUENCE CHARACTERISTICS:
        (A) LENGTH:       22 nucleotides
        (B) TYPE:         nucleic acid
        (C) STRANDEDNESS: single
        (C) TOPOLOGY:     linear (ii) MOLECULE TYPE:    synthetic DNA (iii) SEQUENCE DESCRIPTION:    SEQ ID NO: 14:

GCATTCTGGT AATTTAGTCC AA                                             22

(2) INFORMATION FOR SEQ ID NO:15:

(i) SEQUENCE CHARACTERISTICS:
        (A) LENGTH:       21 nucleotides
        (B) TYPE:         nucleic acid
        (C) STRANDEDNESS: single
        (C) TOPOLOGY:     linear (ii) MOLECULE TYPE:    synthetic DNA (iii) SEQUENCE DESCRIPTION:    SEQ ID NO: 15:

ATTGGATAGC ACTATTTATT A                                              21

(2) INFORMATION FOR SEQ ID NO:16:

(i) SEQUENCE CHARACTERISTICS:
        (A) LENGTH:       20 nucleotides
```

-continued

```
         (B)  TYPE:            nucleic acid
         (C)  STRANDEDNESS:    single
         (C)  TOPOLOGY:        linear (ii) MOLECULE TYPE:        synthetic DNA (iii) SEQUENCE DESCRIPTION:   SEQ ID NO: 16:

ATCAATTCAG AGTCTTACAG                                                  20
```